United States Patent
Lin et al.

(10) Patent No.: US 10,061,733 B2
(45) Date of Patent: Aug. 28, 2018

(54) PERIPHERAL INTERFACE CHIP AND DATA TRANSMISSION METHOD THEREOF

(71) Applicants: Shang-Heng Lin, Taipei (TW); Jiun-Shiue Huang, Taipei (TW); Yu-Hsiang Lee, Taipei (TW)

(72) Inventors: Shang-Heng Lin, Taipei (TW); Jiun-Shiue Huang, Taipei (TW); Yu-Hsiang Lee, Taipei (TW)

(73) Assignee: ITE Tech. Inc., Hsinchu (TW)

( * ) Notice: Subject to any disclaimer, the term of this patent is extended or adjusted under 35 U.S.C. 154(b) by 159 days.

(21) Appl. No.: 15/293,307

(22) Filed: Oct. 14, 2016

(65) Prior Publication Data
US 2018/0024953 A1    Jan. 25, 2018

(30) Foreign Application Priority Data
Jul. 20, 2016    (TW) .............................. 105122833 A

(51) Int. Cl.
G06F 13/40    (2006.01)
G06F 13/42    (2006.01)
G06F 13/10    (2006.01)
G06F 13/38    (2006.01)
A61B 5/00    (2006.01)
G06F 13/24    (2006.01)

(52) U.S. Cl.
CPC ........ G06F 13/4022 (2013.01); G06F 13/102 (2013.01); G06F 13/385 (2013.01); G06F 13/4282 (2013.01); G06F 13/4295 (2013.01); A61B 5/7475 (2013.01); G06F 13/24 (2013.01)

(58) Field of Classification Search
CPC ............. G06F 13/4022; G06F 13/4282; G06F 13/102; A61B 5/7475
See application file for complete search history.

(56) References Cited

U.S. PATENT DOCUMENTS

| 6,912,663 | B1 * | 6/2005 | Dayan ................ G06F 13/4295 361/679.08 |
| 8,872,777 | B2 | 10/2014 | Lee |
| 2011/0264942 | A1 | 10/2011 | Tsukamoto |
| 2014/0181479 | A1 | 6/2014 | Sasanka |
| 2015/0026367 | A1 * | 1/2015 | Yen ........................ G06F 21/44 710/16 |

FOREIGN PATENT DOCUMENTS

| TW | M471621 | 2/2014 |
| TW | M5015922 | 5/2015 |

OTHER PUBLICATIONS

"Office Action of Taiwan Counterpart Application," dated Apr. 25, 2017, p. 1-7.

* cited by examiner

*Primary Examiner* — Ernest Unelus
(74) *Attorney, Agent, or Firm* — JCIPRNET

(57) ABSTRACT

A peripheral interface chip and a data transmission method thereof are provided. The peripheral interface chip includes a switching circuit, a universal serial bus (USB) host controller, a keyboard controller and a microprocessor. The switching circuit receives a device identification transmitted from a USB device, and the device identification is used for determining whether the USB device is a keyboard device. When the USB device is the keyboard device, input data of the USB device is transmitted to a controller hub through a first USB interface, the switching circuit, the USB host controller, the microprocessor, the keyboard controller and a low pin count (LPC) interface.

13 Claims, 3 Drawing Sheets

PERIPHERAL INTERFACE CHIP AND DATA TRANSMISSION METHOD THEREOF

CROSS-REFERENCE TO RELATED APPLICATION

This application claims the priority benefit of Taiwan application serial no. 105122833, filed on Jul. 20, 2016. The entirety of the above-mentioned patent application is hereby incorporated by reference herein and made a part of this specification.

BACKGROUND

Field of the Invention

The invention is directed to a chip and more particularly, to a peripheral interface chip and a data transmission method thereof.

Description of Related Art

A universal serial bus (USB) is a connection interface applied to connect desktop computers, notebook computers, smart phones and tablet PCs with peripheral devices. With a hot swapping characteristic of the USB interface, a user can freely add or remove a peripheral device. Thus, the USB interface has been widely used in peripheral devices, such as keyboards, mice, networks and printers. However, the USB interfaces perform data accessing with the peripheral device through polling, which results in limitation in a keyboard report rate and affection to the users' experience.

SUMMARY

The invention provides a peripheral interface chip and a data transmission method thereof capable of preventing a report rate of a keyboard device from being influenced due to being limited by a universal serial bus (USB) interface.

A peripheral interface chip of the invention includes a switching circuit, a USB host controller, a keyboard controller and a microprocessor. The switching circuit is coupled to a USB device through a first USB interface and coupled to a controller hub through a second USB interface. The USB host controller is coupled to the switching circuit. The keyboard controller is coupled to the controller hub through a low pin count (LPC) interface. The microprocessor is coupled to the USB host controller and the keyboard controller. The switching circuit receives a device identification transmitted from the USB device. The device identification is used for determining whether the USB device is a keyboard device. When the USB device is a keyboard device, input data of the USB device is transmitted to a controller hub through the first USB interface, the switching circuit, the USB host controller, the microprocessor, the keyboard controller and the LPC interface.

A data transmission method of a peripheral interface chip of the invention includes the following steps. A device identification transmitted from a USB device is received by a switching circuit. The device identification is used for determining whether the USB device is a keyboard device. When the USB device is a keyboard device, the input data of the USB device is transmitted to the controller hub through a first USB interface, the switching circuit, a USB host controller, a microprocessor, a keyboard controller and an LPC interface. When the USB device is not the keyboard device, the input data of the USB device is transmitted to the controller hub through the first USB interface, the switching circuit and the second USB interface.

To sum up, in the peripheral interface chip and the data transmission method thereof provided by the invention, whether the USB device is the keyboard device is determined, and the input data of the USB device is transmitted through the LPC interface when the USB device is the keyboard device. Thereby, the LPC interface can notify the controller hub through an interrupt request, and thus, the issue of the limitation in the report rate caused by polling does not occur. Namely, the report rate of the keyboard device can be increased in a condition of matching software and hardware.

To make the above features and advantages of the invention more comprehensible, embodiments accompanied with drawings are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
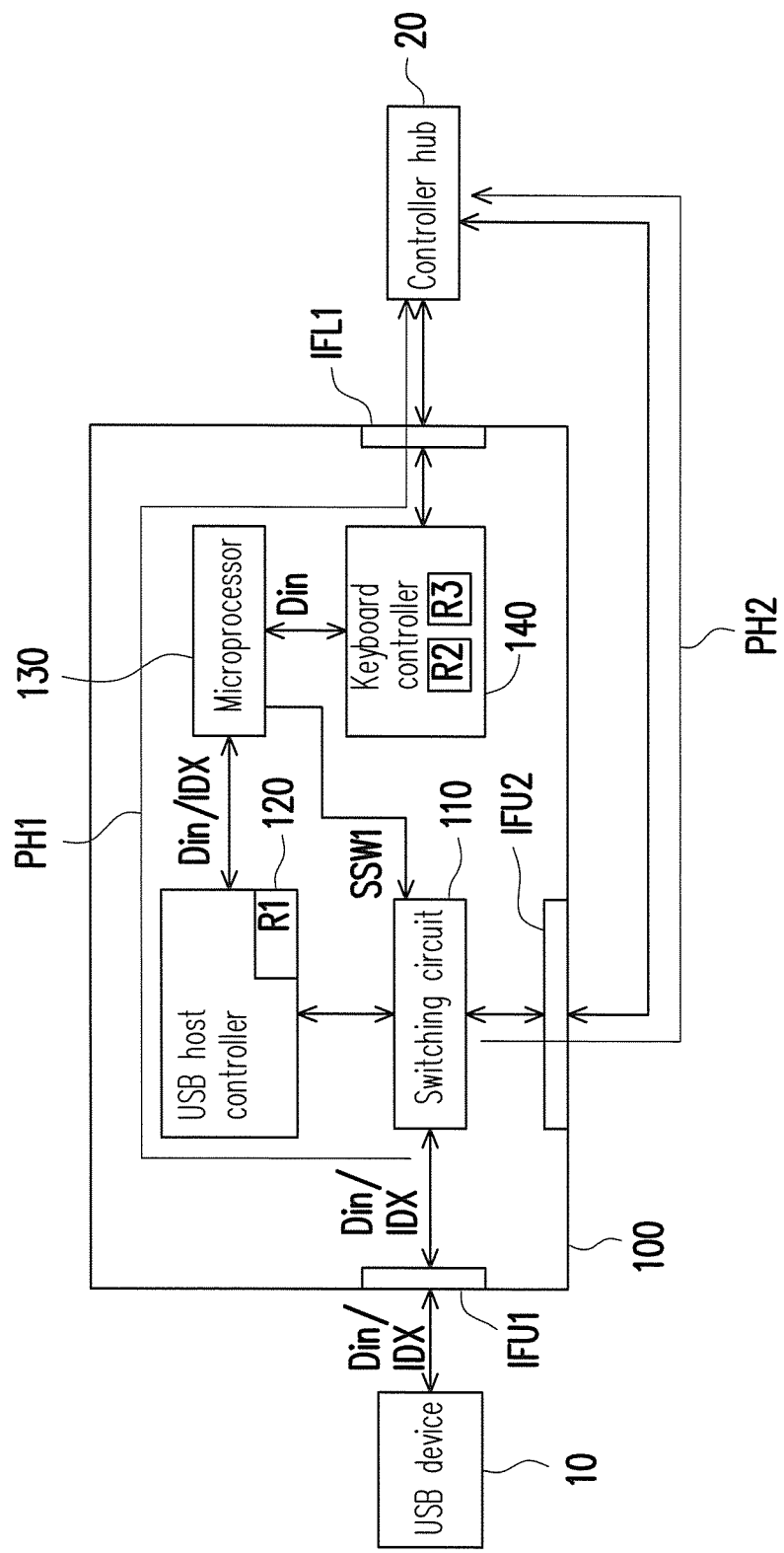
FIG. 1 is a schematic system diagram of a peripheral interface chip according to an embodiment of the invention.

FIG. 1 is a schematic system diagram of a peripheral interface chip according to an embodiment of the invention. Referring to FIG. 1, in the present embodiment, a peripheral interface chip 100 is coupled to a universal serial bus (USB) device 10 and a controller hub 20 and configured to connect the USB device 10 with the controller hub 20. Namely, the peripheral interface chip 100 is employed as a communication medium of the USB device 10 and the controller hub 20. The controller hub 20 is, for example, a platform controller hub (PCH).

The peripheral interface chip 100 includes a first USB interface IFU1, a second USB interface IFU2, a low pin count (LPC) interface IFL1, a switching circuit 110, a USB host controller 120, a microprocessor 130 and a keyboard controller 140. The switching circuit 110 is coupled to the USB device 10 through the first USB interface IFU1 and coupled to the controller hub 20 through the second USB interface IFU2. The USB host controller 120 is coupled to the switching circuit 110. The microprocessor 130 is coupled to the USB host controller 120 and the keyboard controller 140. The keyboard controller 140 is coupled to the controller hub 20 through the LPC interface IFL1.

In the present embodiment, the switching circuit 110 is coupled to the first USB interface IFU1 and the USB host controller 120 by default. When the USB device 10 is coupled to the first USB interface IFU1 and receives a power, the USB device 10 is turned on and provides a device identification IDX to the first USB interface IFU1. The device identification IDX is used for determining whether the USB device 10 is a keyboard device.

When the switching circuit 110 receives the device identification IDX transmitted from the USB device 10, the switching circuit 110 transmits the device identification IDX of the USB device 10 to the USB host controller 120. When the microprocessor 130 reads the device identification IDX from the USB host controller 120, the microprocessor 130 determines whether the USB device 10 is a keyboard device according to the device identification IDX transmitted from the USB device 10 to correspondingly provide a switching signal SSW1 to the switching circuit 110.

When the USB device 10 is the keyboard device, the switching circuit 110 is controlled by the switching signal SSW1 to couple the first USB interface IFU1 with the USB host controller 120, as illustrated by a path PH1. An information packet (including input data Din) of the USB device 10 is transmitted to the controller hub 20 through the first USB interface IFU1, the switching circuit 110, the USB host controller 120, the microprocessor 130, the keyboard controller 140 and the LPC interface IFL1. When the USB device 10 is not the keyboard device, the switching circuit 110 is controlled by the switching signal SSW1 to couple the first USB interface IFU1 with the second USB interface IFU2, as illustrated by a path PH2. The information packet (including the input data Din) of the USB device 10 is transmitted to the controller hub 20 through the first USB interface IFU1, the switching circuit 110 and the second USB interface IFU2.

Furthermore, when the USB device 10 is the keyboard device, the switching circuit 110 transmits the information packet (including the input data Din) of the USB device 10 to the USB host controller 120. Then, the USB hot controller 120 extracts the input data Din from the information packet, i.e., performs a decoding operation on the input data Din, and stores it in a register set R1 of the USB host controller 120 (i.e., correspondingly stores the decoded input data Din in a plurality of registers). After confirming that the register set R1 is used (i.e., the input data Din is written therein), the microprocessor 130 writes the input data Din stored in the register set R1 into a register R2 (referred to as a first register) corresponding to a data port and a register R3 (refereed to as a second register) corresponding to an instruction port in the keyboard controller 140. Then, the USB hot controller 20 reads the input data Din from the registers R2 and R3.

In an embodiment of the invention, when the USB device 10 is the keyboard device, an address of the register R2 is, for example, 0x60, an address of the register R3 is, for, example, 0x64, and the keyboard controller 140 may notify the controller hub 20 through an interrupt request. Meanwhile, when the USB host controller 120 receives the information packet (including the input data Din) from the USB device 10, the USB host controller 120 first notifies the microprocessor 130, and then, the microprocessor 130 induces the USB host controller 120 to read the information packet (including the input data Din) transmitted by the switching circuit 110 through setting an operation parameter of the USB host controller 120. And, the microprocessor 130 makes the keyboard controller 140 connected with the controller hub 20 and the keyboard controller 140 operating through setting the operation parameter and through the data port (e.g., the register having the address of 0x60) and the instruction port (e.g., the register having the address of 0x64) of the keyboard controller 140.

Figure 2:
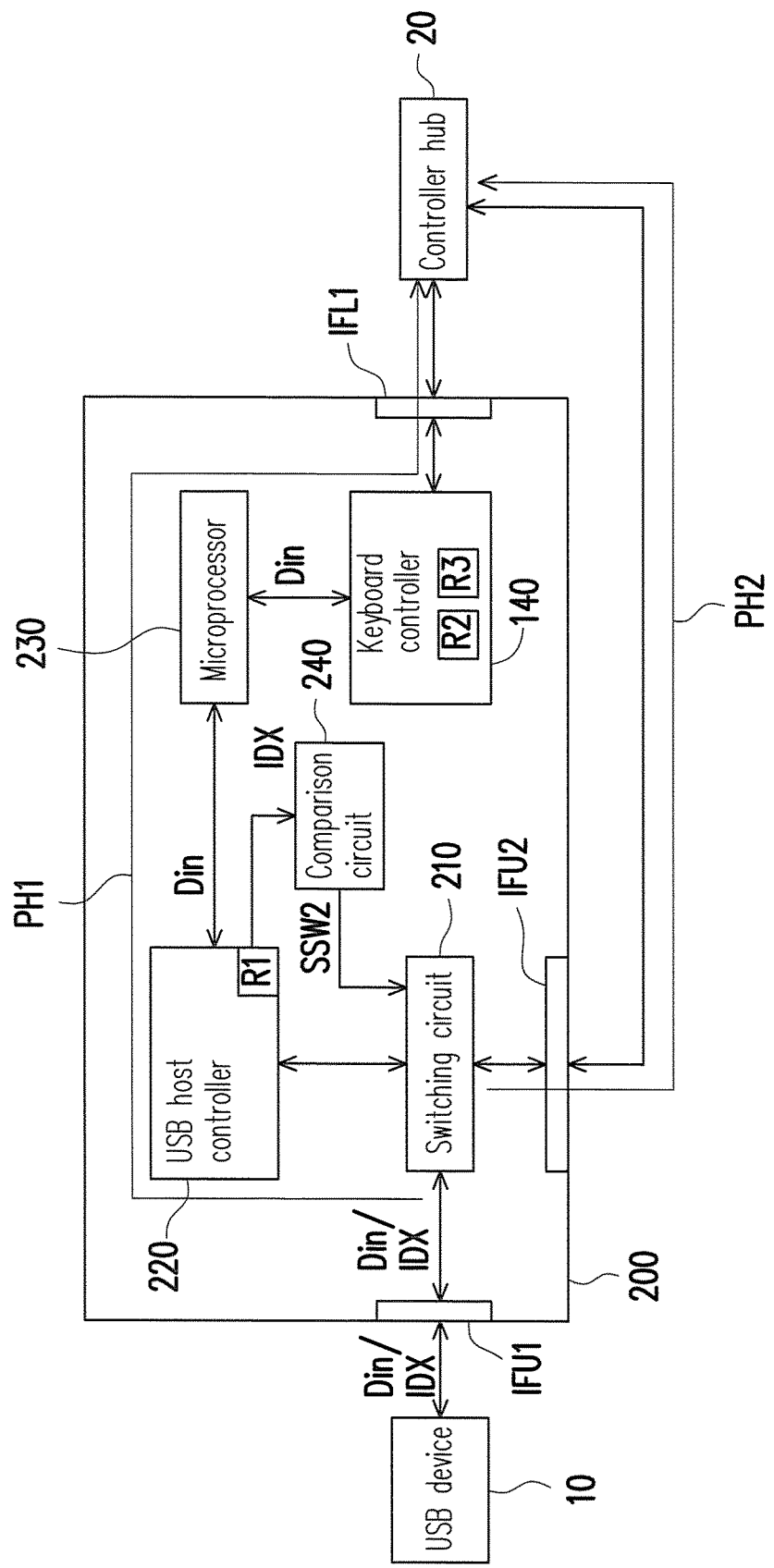
FIG. 2 is a schematic system diagram of a peripheral interface chip according to another embodiment of the invention.

FIG. 2 is a schematic system diagram of a peripheral interface chip according to another embodiment of the invention. Referring to FIG. 1 and FIG. 2, a peripheral interface chip 200 of the present embodiment is substantially the same as the peripheral interface chip 100, and a difference therebetween lies in the peripheral interface chip 200 including a switching circuit 210, a USB host controller 220, a microprocessor 230 and a comparison circuit 240. The comparison circuit 240 is coupled to the USB host controller 220 and the switching circuit 210. In the present embodiment, the switching circuit 210 is still coupled to the first USB interface IFU1 and the USB host controller 220 by default. Thus, the device identification IDX is transmitted to the comparison circuit 240 through the USB host controller 220, and the comparison circuit 240 determines whether the USB device 10 is the keyboard device according to the device identification IDX to correspondingly provide a switching signal SSW2 to the switching circuit 210. In addition, the microprocessor 230 is operated similarly to the microprocessor 130, but does not provide the switching signal SSW2 to the switching circuit 210.

When the USB device 10 is determined as the keyboard device, the switching circuit 210 is controlled by the switching signal SSW2 to couple the first USB interface IFU1 with the USB host controller 220. When the USB device 10 is determined as not the keyboard device, the switching circuit 210 is controlled by the switching signal SSW2 to couple the first USB interface IFU1 with the second USB interface IFU2.

Figure 3:
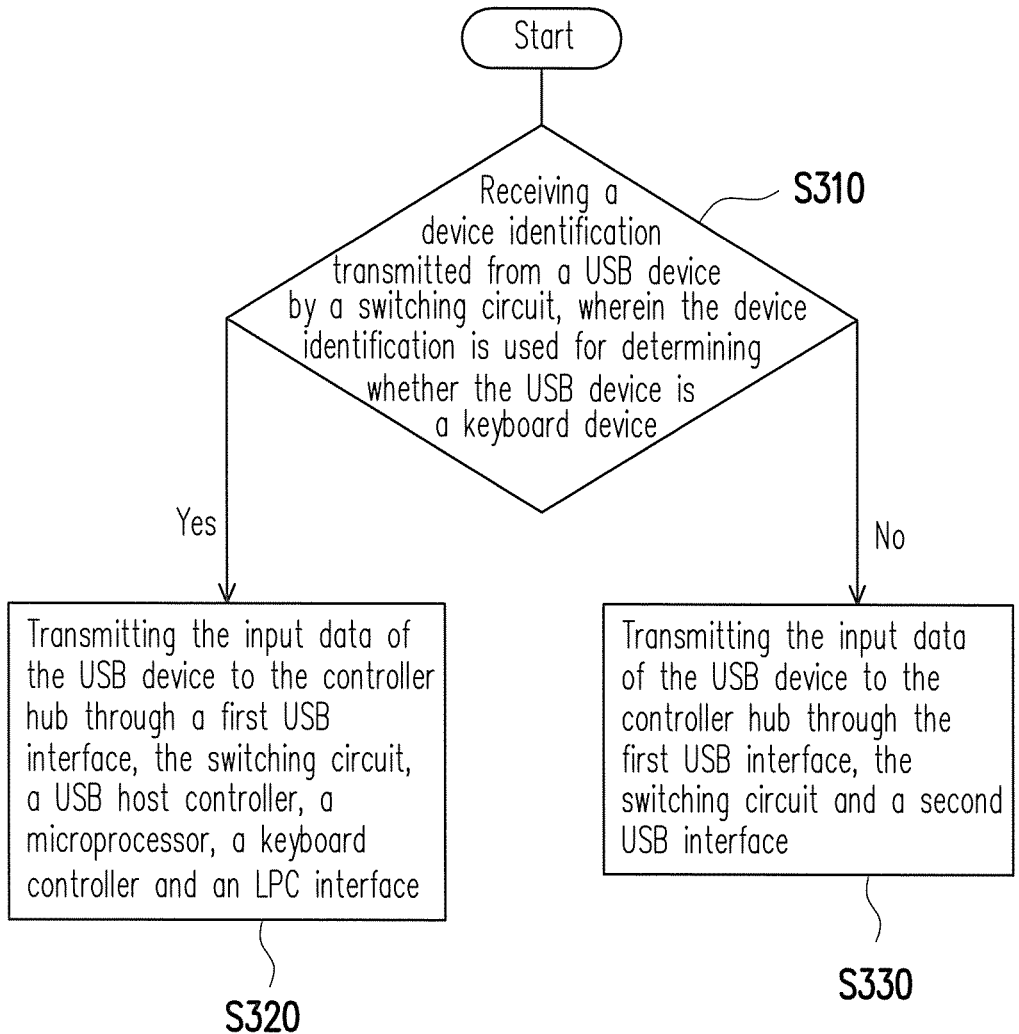
FIG. 3 is a schematic flowchart of a data transmission method of a peripheral interface chip according to an embodiment of the invention.

FIG. 3 is a schematic flowchart of a data transmission method of a peripheral interface chip according to an embodiment of the invention. Referring to FIG. 3, in the present embodiment, a data transmission method of a peripheral interface chip of the invention includes the following steps. In step S310, a device identification transmitted from a USB device is received by a switching circuit. The device identification is used for determining whether the USB device is a keyboard device. When the USB device is the keyboard device, i.e., the determination result of step 310 is "yes", input data of the USB device is transmitted to a controller hub through a first USB interface, the switching circuit, a USB host controller, a microprocessor, a keyboard controller and an LPC interface (step S320). When the USB device is not the keyboard device, i.e., the determination result of step 310 is "no", the input data of the USB device is transmitted to the controller hub through the first USB interface, the switching circuit and a second USB interface (step S330). Herein, the sequence of steps S310, S320 and S330 are for description, and the embodiments of the invention are not limited thereto. In the meantime, details of steps S310, S320 and S330 may refer to the description with respect to the embodiments illustrated in FIG. 1 and FIG. 2, and will not repeated hereinafter.

Based on the above, in the peripheral interface chip and the data transmission method thereof provided by the invention, whether the USB device is the keyboard device is determined, and the input data of the USB device is transmitted through the LPC interface when the USB device is the keyboard device. Thereby, the LPC interface can notify the controller hub through the interrupt request, and thus, the issue of the limitation in the report rate caused by polling does not occur. Namely, the report rate of the keyboard device can be increased in a condition of matching software and hardware.

Although the invention has been disclosed by the above embodiments, they are not intended to limit the invention. It will be apparent to one of ordinary skill in the art that modifications and variations to the invention may be made without departing from the spirit and scope of the invention. Therefore, the scope of the invention will be defined by the appended claims.

What is claimed is:

1. A peripheral interface chip, comprising:
a switching circuit, coupled to a universal serial bus (USB) device through a first USB interface and coupled to a controller hub through a second USB interface;
a USB host controller, coupled to the switching circuit;
a keyboard controller, coupled to the controller hub through a low pin count (LPC) interface; and
a microprocessor, coupled to the USB host controller and the keyboard controller,
wherein the switching circuit receives a device identification transmitted from the USB device, the device identification is used for determining whether the USB device is a keyboard device, and when the USB device is the keyboard device, the input data of the USB device is transmitted to the controller hub through the first USB interface, the switching circuit, the USB host controller, the microprocessor, the keyboard controller and the LPC interface,
wherein when the USB device is the keyboard device, the switching circuit transmits the input data of the USB device to the USB host controller, so as to store the input data in a register set of the USB host controller, and after confirming that the register set is used, the microprocessor writes the input data stored in the register set into a first register corresponding to a data port and a second register corresponding to an instruction port in the keyboard controller, such that the controller hub reads the input data from the first register and the second register.

2. The peripheral interface chip according to claim 1, wherein an address of the first register is 0x60, and an address of the second register is 0x64.

3. The peripheral interface chip according to claim 1, wherein the keyboard controller notifies the controller hub through an interrupt request.

4. The peripheral interface chip according to claim 1, wherein when the USB device is not the keyboard device, the input data of the USB device is transmitted to the controller hub through the first USB interface, the switching circuit and the second USB interface.

5. The peripheral interface chip according to claim 1, wherein the controller hub is a platform controller hub (PCH).

6. The peripheral interface chip according to claim 1, wherein the microprocessor reads the device identification from the USB host controller and determines whether the USB device is the keyboard device, wherein the microprocessor provides a switching signal to the switching circuit according to whether the USB device is the keyboard device.

7. The peripheral interface chip according to claim 1, further comprising: a comparison circuit, wherein the device identification is transmitted to the comparison circuit through the switching circuit and the USB host controller, and the comparison circuit determines whether the USB device is the keyboard device, wherein the comparison circuit provides a switching signal to the switching circuit according to whether the USB device is the keyboard device.

8. A data transmission method of a peripheral interface chip, comprising:
receiving a device identification transmitted from a universal serial bus (USB) device by a switching circuit, wherein the device identification is used for determining whether the USB device is a keyboard device;
when the USB device is the keyboard device, transmitting the input data of the USB device to the controller hub through a first USB interface, the switching circuit, a USB host controller, a microprocessor, a keyboard controller and a low pin count (LPC) interface;
when the USB device is not the keyboard device, transmitting the input data of the USB device to the controller hub through the first USB interface, the switching circuit and a second USB interface; and
when the USB device is the keyboard device, transmitting the input data of the USB device to the USB host controller by the switching circuit, so as to store the input data in a register set of the USB host controller, writing the input data stored in the register set into a first register corresponding to a data port and a second register corresponding to an instruction port in the keyboard controller by the microprocessor after confirming that the register set is used, such that the controller hub reads the input data from the first register and the second register.

9. The data transmission method of the peripheral interface chip according to claim 8, wherein an address of the first register is 0x60, and an address of the second register is 0x64.

10. The data transmission method of the peripheral interface chip according to claim 8, wherein the keyboard controller notifies the controller hub through an interrupt request.

11. The data transmission method of the peripheral interface chip according to claim 8, wherein the controller hub is a platform controller hub (PCH).

12. The data transmission method of the peripheral interface chip according to claim 8, further comprising:
reading the device identification from the USB host controller by the microprocessor, and determines whether the USB device is the keyboard device by the microprocessor, wherein the microprocessor provides a switching signal to the switching circuit according to whether the USB device is the keyboard device.

13. The data transmission method of the peripheral interface chip according to claim 8, further comprising:
transmitting the device identification to a comparison circuit by the USB host controller, and determining whether the USB device is the keyboard device by the comparison circuit, wherein the comparison circuit provides a switching signal to the switching circuit according to whether the USB device is the keyboard device.

* * * * *